United States Patent [19]
Krenmueller et al.

[11] 3,931,253
[45] Jan. 6, 1976

[54] PROCESS FOR THE PRODUCTION OF AMINOANTHRAQUINONE

[75] Inventors: Franz Krenmueller; Heinrich Till, Kufstein, Tirol, both of Austria

[73] Assignee: Sandoz Ltd., (Sandoz AG), Basel, Switzerland

[22] Filed: Aug. 6, 1973

[21] Appl. No.: 385,758

[52] U.S. Cl. .................................................. 260/378
[51] Int. Cl.² .......................................... C09B 1/20
[58] Field of Search ...................................... 260/378

[56] References Cited
FOREIGN PATENTS OR APPLICATIONS
705,919   3/1954   United Kingdom................. 260/378

OTHER PUBLICATIONS
Parrett et al., Journal of the American Chemical Society, Vol. 48, pp. 778–782, (1926).

Weygand/Hilgetag, Preparative Organic Chemistry, pp. 557–560, (1972).

Corey (ED.), Organic Synthesis, Vol. 46, pp. 85–89, (1966).

*Primary Examiner*—Lorraine A. Weinberger
*Assistant Examiner*—E. Jane Skelly
*Attorney, Agent, or Firm*—Gerald D. Sharkin; Richard E. Vila; Joseph J. Borovian

[57] ABSTRACT

The present invention concerns a novel process for the production of an aminoanthraquinone, which comprises catalytically hydrogenating the corresponding nitroanthraquinone in an organic solvent. Aminoanthraquinones are known and are useful as intermediates in the production of anthraquinone dyestuffs.

23 Claims, 1 Drawing Figure

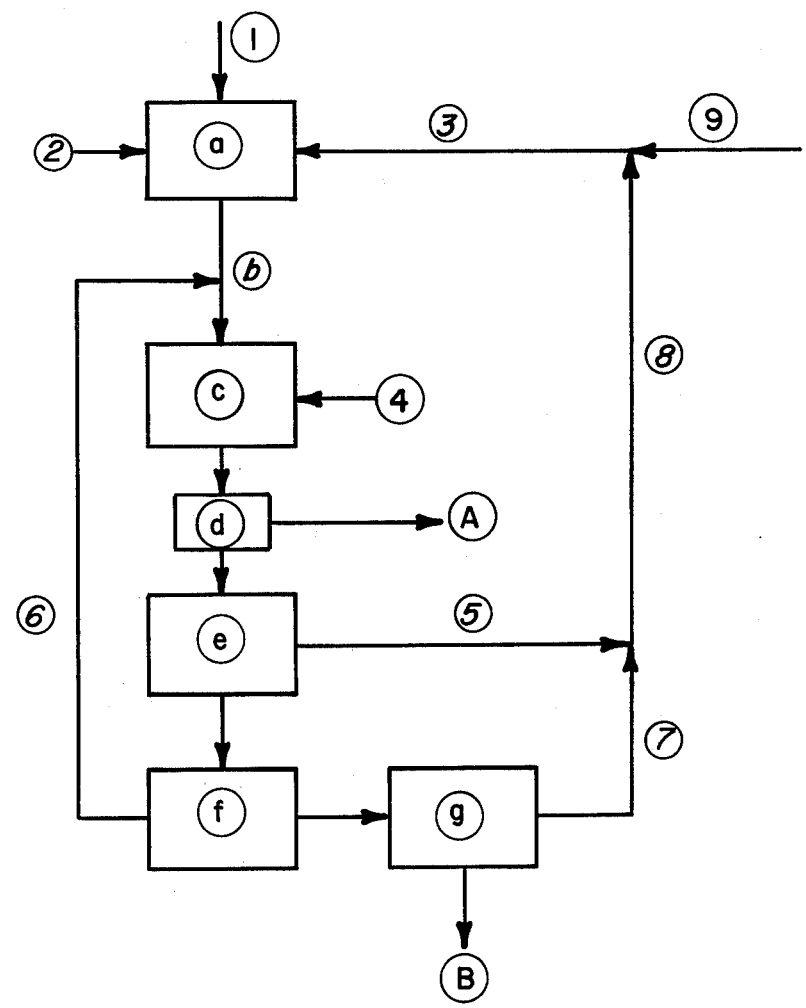

PROCESS FOR THE PRODUCTION OF AMINOANTHRAQUINONE

IMPROVEMENTS IN OR RELATING TO ORGANIC COMPOUNDS

The present invention relates to aminoanthraquinones and more specifically to a process for the production of aminoanthraquinones.

Aminoanthraquinones, in particular 1-aminoanthraquinone, are important intermediates in the synthesis of anthraquinone dyes. For such use, it is of importance to obtain the aminoanthraquinones in high yield and purity.

Accordingly, the present invention provides a process for the production of an aminoanthraquinone from a nitroanthraquinone, which comprises hydrogenating the nitroanthraquinone in the presence of a solid hydrogenation catalyst and in an inert organic solvent in which the resulting aminoanthraquinone is soluble and the catalyst insoluble, and removing the catalyst from the resulting aminoanthraquinone solution.

According to a preferred aspect of the present invention the inert solvent is such that the resulting aminoanthraquinone is soluble therein at an upper temperature and insoluble therein at a lower temperature, the catalyst being removed at the upper temperature.

The difference in temperature between the upper and lower temperatures is preferably from 40° to 150°C, e.g. from 50° to 130°C, more preferably from 60° to 125°C especially from 70° to 125°C, and conveniently said lower temperature is room temperature. As will be appreciated, in general, the solvent is preferably selected such that the temperature solubility gradient thereof in relation to the aminoanthraquinone (i.e., the rate of increase of solubility of the aminoanthraquinone with increase of temperature) is as large as possible. In addition the inert solvent is preferably such that any over-hydrogenated aminoanthraquinone that may be formed by over-hydrogenation of the resulting aminoanthraquinone is soluble therein at said lower temperature, and after removal of the catalyst at the upper temperature, the solution is cooled to the lower temperature and the aminoanthraquinone is removed from the solution. Preferably the nitroanthraquinone is hydrogenated in excess of the theoretical amount of hydrogen so that a small proportion of the resulting aminoanthraquinone is overhydrogenated to overhydrogenated aminoanthraquinone (believed to be nuclear hydrogenated aminoanthraquinone), e.g. 7 percent especially between 0.5 and 6 percent by weight, of the resulting aminoanthraquinone, is overhydrogenated. In further accordance with this preferred aspect of the invention, after removal of the resulting aminoanthraquinone, the nuclear-hydrogenated aminoanthraquinone remaining in solution is oxidised to aminoanthraquinone, conveniently by reaction with nitroanthraquinone or a nitrohydrogenated derivative thereof of higher oxidative level than aminoanthraquinone, e.g. hydroxylaminoanthraquinone. One method of achieving oxidation of the nuclear-hydrogenated aminoanthraquinone is by recycling the final solution containing the nuclear-hydrogenated aminoanthraquinone, after removal of the aminoanthraquinone, into the initial reaction mixture containing the nitroanthraquinone and proceeding with hydrogenation. In this manner, the recycled nuclear hydrogenated aminoanthraquinone is allowed to react with the nitroanthraquinone or its hydrogenated derivatives of higher oxidative level than the aminoanthraquinone, i.e., with nitroanthraquinone, nitrosoanthraquinone or hydroxylaminoanthraquinone, and thereby be oxidised with simultaneous reduction of the nitroanthraquinone or its hydrogenated derivative. Such recycling of the final reaction solution after removal of the catalyst and then the aminoanthraquinone lends itself particularly to continuous operation of the process of the invention, by continuously recycling with addition of nitroanthraquinone starting material and catalyst, and replenishing with solvent, as necessary.

It will, however, be appreciated that the present invention lends itself not only to continuous operation, but also to semi-continuous or discontinuous operation e.g. batch production.

The nitroanthraquinone employed as starting material may, for example, be a mononitro or dinitroanthraquinone such as 1-nitroanthraquinone, 2-nitroanthraquinone, 1,2-dinitroanthraquinone, 1,6-dinitroanthraquinone, 1,7-dinitroanthraquinone, 1,8-dinitroanthraquinone, 1,5-dinitroanthraquinone, 2,7-dinitroanthraquinone or 2,6-dinitroanthraquinone.

In addition the anthraquinone may comprise a single nitroanthraquinone or a mixture of nitroanthraquinone constituents. Preferably however, one nitroanthraquinone at least predominates and, for example, in the case of 1-nitroanthraquinone, preferably the 1-nitroanthraquinone predominates to at least 85 percent, more preferably at least 90 percent, e.g. 95–100 percent by weight. Moreover, it is not essential that the nitroanthraquinone employed as starting material be completely free from impurities and, for example, crude nitroanthraquinones obtained by nitration of anthraquinone and containing the impurities normally associated with this manner of production, e.g. small amounts of anthraquinone, may be employed as starting material in the process of the invention.

Suitable inert organic solvents are those which do not react with the starting, intermediate or final compounds and which are not subject to hydrogenation under the conditions of the reaction. In addition, and where necessary, solvents should fulfill the selective solubility requirements, e.g. as between the resulting aminoanthraquinone and the nuclear hydrogenated aminoanthraquinone, insofar as this is required. As example of suitable solvents, there may be mentioned liquid substituted or unsubstituted aromatic hydrocarbons such as an aromatic hydrocarbon petroleum fraction, e.g. having a boiling range of 170° to 200°C, xylene, e.g. m-xylene, toluene or chlorobenzene. Further examples of suitable solvents that may be mentioned are liquid ethers particularly arylalkyl ethers such as alkyl ($C_1$-$C_5$) ethers of phenol, which may be mono or polyalkyl substituted with a total of 1 to 6 carbon atoms in the alkyl substituents, or of dihydroxybenzene, in particular anisole, phenetol, hydroquinone dimethylether and resorcinol dimethylether. Aliphatic ethers may also be mentioned such as dialkylethers, e.g. di-n-butylether, or, preferably, mono or diethers of glycols, particularly derived from glycols of 2 to 4 carbon atoms or diethylene or triethylene glycols with aliphatic alcohols of 1 to 5 carbon atoms, especially diethylene glycol dimethylether, diethylene glycol monoethyl ether, ethylene glycol, monoethyl ether and ethylene glycol dimethylether. Further ethers that may be mentioned are cyclic ethers such as dioxan or tetrahydrofuran. Other examples of suitable solvents that may be employed are carboxylic acid esters such as esters derived from aromatic acids, e.g. unsubstituted or substituted benzoic acid or aliphatic carboxylic acids with aliphatic alcohols ($C_1$-$C_5$), with glycols ($C_2$-$C_4$) or with cyclohexanol, in particular adipic diethyl ester, ethyl benzoate, cyclohexylacetate, ethyl 0-ethylsalicylate and ethylene glycol monoacetate.

For the production of 1-aminoanthraquinone, the liquid aryl-alkyl ethers, especially anisole and phenetol, are preferred.

The amount of solvent employed is, advantageously, as little as possible, particularly when selective solubility as between the resulting aminoanthraquinone and the nuclear hydrogenated aminoanthraquinone is desired. Preferably, the ratio by weight of the amount of solvent to the amount of nitroanthraquinone is in the range 100:1 to 1:2, more preferably in the range 20:1 to 1:1.

The nitroanthraquinone may either be dissolved in the solvent, or may be suspended therein, preferably the former. In addition, as will be appreciated, it is not essential that the resulting aminoanthraquinone passes directly into solution immediately on its formation. It may, for example, precipitate out and later be dissolved by heating towards the end of the reaction.

As suitable hydrogenation catalysts, metal hydrogenation catalysts, preferably employed in finely dispersed form, offering as large an active surface as possible, may be employed, particularly noble metal catalysts, e.g. palladium, platinum, ruthenium and rhodium, which may be employed with a carrier such as barium sulphate, strontium carbonate, calcium carbonate, silicon dioxide, aluminium sesquioxide and particularly active charcoal. Nickel catalysts e.g. Raney nickel, may also be mentioned.

The amount of catalyst employed in the process of the invention is suitably 0.05 to 10 percent of the weight of nitroanthraquinone (including the weight of any catalyst carrier) and preferably 0.1 to 5 percent by weight.

The process of the invention is preferably effected with heating, e.g. to a temperature of up to 200°C, such as between 50° to 200°C, in particular from 80° to 160°C.

The hydrogen partial pressure may be up to 15 atmospheres, e.g. between 0.5 and 15 atmospheres, preferably between 0.5 and 10 atmospheres.

Naturally, the actual temperature and hydrogen partial pressure employed will depend on the nature and composition of the nitroanthraquinone employed as starting material, and also the solvent. Thus, when 1-nitroanthraquinone of at least 85 percent by weight purity is employed in an aryl-alkyl ether solvent, the preferred temperature is from 80° – 170°C more preferably from 100° to 150°C, and the partial pressure is preferably 0.5 to 10 atmospheres, more preferably 1 to 7 atmospheres.

The hydrogenation in accordance with the process of the invention is found in general to proceed with almost complete reaction of the hydrogen so that an almost stoichiometric quantity of hydrogen is consumed. The progress of the reaction may therefore be acceptably monitored on the basis of the amount of hydrogen employed. When the progress of the reaction is monitored chromatographically, in the view of the rather rapid rate of hydrogenation, the supply of hydrogen to the reaction mixture is preferably interrupted temporarily to terminate the reaction when chromatographic determinations are being effected.

After the completion of the reaction, the spent hydrogenation catalyst is removed from the resulting aminoanthraquinone solution, if necessary at an elevated temperature to dissolve the aminoanthraquinone, e.g. by filtration or by centrifuging. After removal of the spent catalyst, the resulting aminoanthraquinone may be removed from the solution, if necessary after concentration of the solution and reducing the temperature, by crystallization and filtration. Alternatively, and especially in the case where substantially pure aminoanthraquinone is obtained, the resulting solution may be evaporated to dryness.

In one mode of effecting the process of the invention, particularly suitable for continuous and semicontinuous production of aminoanthraquinones, the nitroanthraquinone is dissolved or suspended in the inert organic solvent in a mixing and heating chamber and the catalyst added. The temperature of the mixture is then raised until the desired temperature has been reached. The hot mixture is then passed to a reaction chamber where hydrogen is blown therethrough, the reaction being effected adiabatically, isothermally or, if necessary, with positive or negative temperature adjustment by external heat exchange. After the required degree of hydrogenation, computed on the basis of the rate of hydrogenation, the reaction mixture then passes to a separating chamber where the spent catalyst is removed, e.g. by filtration, under conditions avoiding heat loss to maintain the desired aminoanthraquinone in solution. The solution is then passed to an evaporating chamber where part or all of the solvent is removed. The solvent removed is recovered and recycled. Preferably, however, only part of the solvent is removed, and the concentrated solution is passed to a crystallisor whereupon, with cooling, aminoanthraquinone crystallises and is removed after passage to a filtration chamber. The filtrate cake, consisting of wet aminoanthraquinone, is passed to an evaporator where it is dried, the removed solvent being recovered and recycled. The mother liquor, recovered from the filtration is passed to the initial nitroanthraquinone solvent mixing chamber to be recycled through the apparatus. In the case where overhydrogenation is effected, i.e., in excess of the theoretical amount, so that nuclear hydrogenated aminoanthraquinone is obtained, this recycling of the mother liquor containing the nuclear hydrogenated aminoanthraquinone has the effect of oxidising the nuclear hydrogenated aminoanthraquinone by reaction thereof with nitroanthraquinone starting material or reduction derivatives thereof of higher oxidation level than the nuclear hydrogenated compound. Most economically, overhydrogenation is effected to a distinct but low degree.

Examples of the process of the invention will now be described, in some cases, with reference to the accompanying drawing which shows a schematic flow diagram of a method of performing the present invention. In the following examples, where temperatures are referred to, these are in °C, where pressure is indicated in atmospheres, these are technical atmospheres and where a ratio of parts by volume to parts by weight is given, this is the same as of ml to g. Volumes are measured at STP unless otherwise indicated.

It is understood that where a partial pressure is referred to throughout the specification, an excess pressure, i.e., above atmospheric pressure, is intended unless otherwise indicated.

EXAMPLE 1

1 Part of crude nitroanthraquinone with a content of 90 percent of 1-nitroanthraquinone is dissolved by heating in 25 parts of a petroleum fraction consisting of a mixture of aromatic hydrocarbons having a boiling range of 170°–200°. The solution is treated with 0.1 parts of hydrogenation catalyst (1 percent of Pt on active charcoal) and submitted to hydrogenation in a vessel, thermostatically stabilized at 100°, with fine hydrogen inlet openings in the bottom. After no more 1-nitroanthraquinone can be detected in the reaction solution by means of thin layer chromatography, rinsing is effected with nitrogen and air is passed through for a brief period. The catalyst is separated off and the filtrate cooled down to room temperature, on which 1-aminoanthraquinone is liberated in the form of easily filtrable crystals.

The mother liquor is now separated and the crystallization product dried at 120° and 20 mm of Hg, after washing with a small quantity of cold benzene. 0.75 Parts of a product containing 93 percent of 1-aminoanthraquinone are obtained. By concentrating the mother liquor another 0.12 parts of a less pure product is obtained.

EXAMPLE 2

1 Part of crude nitroanthraquinone with a content of 90 percent of 1-nitroanthraquinone is dissolved by heating in 9 parts of anisole, the solution treated with 0.05 parts of a hydrogenation catalyst (4 percent Pd on active charcoal) and submitted to hydrogenation through fine hydrogen inlet openings in the bottom of a vessel thermostatically stabilized at 130°. After no more 1-nitroanthraquinone is detectable in the reaction solution by means of thin layer chromatography, rinsing is effected with nitrogen and air passed through for a short period. The catalyst is separated and the filtrate cooled down to room temperature, on which 1-aminoanthraquinone is liberated in the form of easily filtrabale crystals. The crystallization product is now separated from the mother liquor, washed with a small quantity of cold benzene and dried at 100° and 20 mm of Hg. 0.82 Parts of a product containing 94 percent of 1-aminoanthraquinone are obtained. By concentration of the mother liquor another 0.05 parts of a less pure product is obtained.

EXAMPLE 3

1 Part of crude nitroanthraquinone with a content of 90 percent of 1-nitroanthraquinone is dissolved by heating in 9 parts of the mother liquor obtained in Example 2, the solution treated with 0.05 parts of hydrogenation catalyst (4 percent of Pd on active charcoal) and submitted to hydrogenation through fine hydrogen inlet openings in the bottom of a vessel thermostatically kept at 130°. After no more 1-nitroanthraquinone is detectable in the reaction solution by means of thin layer chromatography, rinsing is effected with nitrogen and air passed through for a short period. The catalyst is separated and the filtrate cooled down to room temperature, on which 1-aminoanthraquinone is liberated in the form of easily filtrable crystals. The crystallization product is now separated from the mother liquor, washed with a small quantity of cold benzene and dried at 100° and 20 mm of Hg. 0.83 Parts of a product containing 94 percent of 1-aminoanthraquinone are obtained. By concentrating the mother liquor another 0.08 parts of less pure product is obtained.

EXAMPLE 4

1 Part of crude nitroanthraquinone with a content of 90 percent of 1-nitroanthraquinone, 9 parts of phenetol and 0.33 parts of hydrogenation catalyst (2,4 percent Pd on $Al_2O_3$) are heated in an autoclave with a stroke agitator, to 130°. While heating, rinsing is effected with nitrogen which is followed by hydrogen when the final temperature has been reached. The stroke agitator is then activated and hydrogenation effected for 35 minutes at a pressure of 3 atm., upon which the hydrogen is followed by nitrogen, and afterwards by air at 5 atm. The agitator is run for 15 minutes. The catalyst is separated and the filtrate cooled down to room temperature on which 1-aminoanthraquinone precipitates in easily filtrable crystals. The crystallization product is separated, washed with a small quantity of cold benzene and dried at 100° and 20 mm of Hg. 0.775 Parts of a product containing 92 percent of 1-aminoanthraquinone are obtained. By concentrating the mother liquor another 0.09 parts of a less pure product are obtained.

EXAMPLE 5

1 Part of crude nitroanthraquinone obtained by nitration of anthraquinone and composed of 90.0 percent of 1-nitroanthraquinone, 0.5 percent of 2-nitroanthraquinone, 1.0 percent of anthraquinone and 8.0 percent of dinitroanthraquinone, 12 parts of ethyl benzoate and 0.01 parts of catalyst (5 percent of Pd on active charcoal) are heated to 130° in an autoclave with a capacity of 26.7 parts by volume, and equipped with a stroke agitator. While heating is effected, rinsing is done with nitrogen followed by hydrogen when the temperature of 130° is reacted so that the total pressure attains 6.0 kp per $cm^2$. The agitator is now run and hydrogenation effected at the above-mentioned pressure until an amount of hydrogen of 280 parts by volume is taken up. The hydrogen is then followed by nitrogen and the catalyst separated, the filtrate cooled down to room temperature, by which 1-aminoanthraquinone is liberated in the form of easily filtrable crystals. The crystallization product is separated, washed with a small quantity of cold benzene and dried at 100° and 20 mm of Hg. 0.74 Parts of a product containing 92.0 percent of 1-aminoanthraquinone, which corresponds to a yield of 85.9 percent of theory. By concentrating the mother liquor, a further 0.13 percent of a product containing 75 percent of 1-aminoanthraquinone is obtained.

EXAMPLE 6

1 Part of crude nitroanthraquinone obtained by nitration of anthraquinone and composed of 90 percent of 1-nitroanthraquinone. 0.5 percent of 2-nitroanthraquinone, 1.0 percent of anthraquinone and 8.0 percent of dinitroanthraquinone, 24 parts chlorobenzene and 0.01 parts of catalyst (5 percent of Pd on active charcoal) are heated to 120° in an autoclave with a total capacity of 25 parts by volume and equipped with a stroke agitator. While heating, rinsing is effected with nitrogen and on reaching the reaction temperature, hydrogen is passed through such that the total pressure is 6.0 kp per $cm^2$. The agitator is activated and hydrogenation conducted at the above-mentioned pressure until an amount of hydrogen corresponding to 275 parts by volume is taken up. Then the hydrogen is followed by nitrogen and the catalyst separated. The filtrate is cooled down to room temperature, where 1-aminoanthraquinone is liberated in the form of easily filtrable crystals. The crystallization product is separated, washed with a small quantity of cold benzene and dried at 100° and 20 mm of Hg. 0.08 Parts of a product containing 93.0 percent of 1-aminoanthraquinone are obtained, which corresponds to a yield of 93.8 percent of theory. By concentrating the mother liquor, a further 0.06 percent of a product containing 62 percent of 1-aminoanthraquinone is obtained.

EXAMPLE 7

1 Part of nitroanthraquinone with a content of 97.0 percent of 1-nitroanthraquinone, 9 parts of anisole and 0.005 parts of catalyst (10 percent Pd on active charcoal) are heated to 130° in an autoclave with a capacity of 20 parts by volume and equipped with a rotary agitator. While heating, rinsing with nitrogen is effected and, on reaching the reaction temperature, hydrogen is passed through to provide a total pressure of 6.0 kp per cm$^2$, at which the agitator is activated and hydrogenation effected until an amount of hydrogen corresponding to 264 parts by volume is taken up. The hydrogen is now followed by nitrogen and the catalyst separated, the filtrate cooled down to room temperature, when 1-aminoanthraquinone is formed in easily filtrable crystals. The crystallization product is separated, washed with a small quantity of cold benzene and dried at 100° and 20 mm of Hg. 0.83 Parts of a product containing 98.0 percent of 1-aminoanthraquinone are obtained, which corresponds to a yield of 95.1 percent of the theory. By concentrating the mother liquor, a further 0.05 parts of a product containing 71 percent of 1-aminoanthraquinone is obtained.

EXAMPLE 8

1 Part of nitroanthraquinone containing 97.0 percent by weight of 1-nitroanthraquinone, 7 parts of monoethyl ether of diethylene glycol and 0.007 parts of catalyst (10 percent of Pd on active charcoal) are heated to 130° in an autoclave with a capacity of 16.7 parts by volume and equipped with a stroke agitator. While heating, rinsing with nitrogen is effected and, on reaching the reaction temperature, hydrogen is passed through at a partial pressure sufficient to attain a total pressure of 6.0 kp per cm$^2$, at which point the agitator is activated and hydrogenation conducted at the above-mentioned pressure until an amount of hydrogen corresponding to 266 parts by volume is taken up. The hydrogen is then followed by nitrogen and the catalyst separated, the filtrate evaporated and dried at 120° and 10 mm of Hg. 0.87 Parts of a product containing 97.0 percent of 1-aminoanthraquinone are obtained. This corresponds to yield of 98.8 percent of the theory.

EXAMPLE 9

With reference to the drawing, 26 parts of pure 1-nitroanthraquinone, 238 parts of anisole and 0.026 parts of a palladium/charcoal catalyst (5 percent Pd on active charcoal) are mixed with heating in a mixer a until the temperature rises to 110° and the 1-nitroanthraquinone is completely dissolved. The mixture is then fed via a pipeline b to a reactor c where hydrogenation is effected by blowing hydrogen through the solution at a partial pressure of 5 atmospheres, the reaction temperature increasing to, and being maintained at, 150°. Hydrogenation is effected until 4 percent overhydrogenation of the resulting aminoanthraquinone occurs, being determined by the amount of hydrogen consumed. After the reaction has been terminated by interruption of the hydrogen supply, the reaction mixture passes to a separator d where the spent catalyst is separated off by filtration of the warm reaction mixture. The filtrate is led to an evaporator/crystallisor e where the anisole is partly distilled off to concentrate the solution. 183 Parts of anisole are removed in this way and recovered for recycling. At this stage 1-aminoanthraquinone precipitates out. The precipitation increases with cooling. After precipitation the mixture is passed to a separator f and the 1-aminoanthraquinone is filtered off yielding a wet filtration cake and leaving 55 parts of mother liquor. The wet filtration cake is transported to an evaporator g.

The yield of the resulting dry and pure 1-aminoanthraquinone is 96 percent of theory.

With regard to the second cycle of operation, the solvent recovered from the evaporator g is led off via pipeline 7 and combined with solvent recovered from the evaporator/crystalliser which is led along pipeline 5, the combined solvent recovered being fed along pipelines 8 and 3 to the mixer a, the recovered solvent, fed to the mixer, being replenished as necessary via a top-up inlet 9. In a mixer a, the recovered solvent, replenished as necessary, serves as solvent for a new charge of 1-nitroanthraquinone. After addition of a new charge of catalyst, mixing and heating, in analogous manner to that described above in relation to the first cycle, are effected and the mixture then passes to the reactor c via pipeline b. The 55 parts of mother liquor obtained by filtration of the precipitate in the separator f is recycled via pipeline 6 with an inlet to pipeline b. The recycled mother liquor contains overhydrogenated 1-aminoanthraquinone. In this manner, the overhydrogenated product passes with the new charge of reactants, to the reactor and the cycle is repeated. In this manner, the process may be effected continuously.

When effecting the process in the continuous manner, as described above, an overall yield of between 99 and 100 percent of 1-aminoanthraquinone is obtained.

EXAMPLE 10

Proceeding in analogous manner to that described in Example 9, and employing a 6 percent overhydrogenation rate of the aminoanthraquinone, 138 parts of anisole are distilled off in the evaporator/crystalliser e and 100 parts of mother liquor is obtained in the separator f which is recycled.

The yield on the first cycle amounts to 94 percent of theory and on recyclisation, to between 99 and 100 percent of theory.

EXAMPLE 11

300 Parts by weight of anisole are mixed with 27 parts of (97 percent) 1-nitroanthraquinone and 0.2 parts by weight of a palladium/charcoal catalyst (5 percent of Pd on active charcoal) and heated to 130° in an autoclave. At this temperature, hydrogen is blown through until the rate of up-take of the hydrogen has fallen to 10 percent of the original value. At this stage, about 2 percent of overhydrogenated product is present (ascertained by TLC). After interruption of the hydrogen supply, at 130°, 0.4 parts by weight of 1-hydroxylaminoanthraquinone are added and stirring is effected for 30 minutes. The catalyst is separated off at the upper temperature, the filtrate is concentrated and cooled and the 1-aminoanthraquinone is filtered off. No nuclear hydrogenated 1-aminoanthraquinone is present in the mother liquor. 23 Parts of 97 percent pure 1-aminoanthraquinone is obtained.

EXAMPLE 12

The procedure is analogous to that described in Example 11, using:

| | |
|---|---|
| 25 | parts of anisole |
| 5 | parts of 1,5-dinitroanthraquinone (95% purity), and |
| 0.1 | parts of catalyst (5% of Pd on active charcoal), operating at 130°, 10 atm. and for a period of hydrogenation of 120 minutes. |
| Yield: | 3.9 parts of 1,5-diaminoanthraquinone at 94% of purity. |

EXAMPLE 13

The procedure is analogous to that described in Example 11 using:

| | |
|---|---|
| 250 | Parts of anisole |
| 13 | Parts of 1,8-dinitroanthraquinone (96% purity) and |
| 0.13 | parts of catalyst (5% of Pd on active charcoal), operating at 130°, 10 atm. and for a time of hydrogenation of 10 minutes. |
| Yield: | |
| 10 | parts of 1,8-diaminoanthraquinone (96% purity). |

What is claimed is:

1. A process for producing an aminoanthraquinone or a diaminoanthraquinone or mixtures thereof from a nitroanthraquinone selected from the group consisting of 1-nitroanthraquinone, 2-nitroanthraquinone, 1,2-dinitroanthraquinone, 1,6-dinitroanthraquinone, 1,7-dinitroanthraquinone, 1,8-dinitroanthraquinone, 1,5-dinitroanthraquinone, 2,7-dinitroanthraquinone, 2,6-dinitroanthraquinone, and mixtures thereof, comprising the steps of: 1) dissolving said nitroanthraquinone in an inert organic solvent selected from the group consisting of a liquid substituted or unsubstituted aromatic hydrocarbon, a liquid ether and a liquid carboxylic acid ester, the weight ratio of solvent to nitroanthraquinone being between 100:1 and 1:2, 2) adding to said mixture, based on the weight of nitroanthraquinone, between 0.05 percent and 10 percent of a metal hydrogenation catalyst selected from the group consisting of noble metal and Raney nickel; 3) heating the resultant mixture to an upper temperature of between 50° and 200°C.; 4) hydrogenating the resultant heated mixture with molecular hydrogen at a partial pressure between 0.5 and 15 atmospheres, while maintaining said upper temperature; 5) separating the undissolved spent catalyst at said upper temperature from the reaction mixture containing dissolved aminoanthraquinone; 6) cooling the reaction mixture to a lower temperature to precipitate the aminoanthraquinone, said lower temperature being between 40° and 150°C. below the upper temperature; and 7) recovering the precipitated aminoanthraquinone, said process characterized in that the inert solvent is such that the resulting aminoanthraquinone is soluble therein at an upper temperature and insoluble therein at a lower temperature, the catalyst being removed at the upper temperature.

2. The process of claim 1 wherein said nitroanthraquinone is selected from the group consisting of 1-nitroanthraquinone, 2-nitroanthraquinone, or a mixture thereof.

3. The process of claim 1 wherein said nitroanthraquinone is selected from the group consisting of 1,2-dinitroanthraquinone, 1,5-dinitroanthraquinone, 1,6-dinitroanthraquinone, 1,7-dinitroanthraquinone, 1,8-dinitroanthraquinone, 2,6-dinitroanthraquinone, 2,7-dinitroanthraquinone, or a mixture thereof.

4. The process of claim 1 wherein said nitroanthraquinone comprises a mixture of mononitroanthraquinone and dinitroanthraquinone.

5. The process of claim 2, wherein a single compound or a mixture in which a single compound predominates is used.

6. The process of claim 5, wherein 1-nitroanthraquinone is used and predominates to at least 85 percent by weight.

7. The process of claim 1, wherein the inert organic solvent is a liquid substituted or unsubstituted aromatic hydrocarbon.

8. The process of claim 7, wherein the inert organic solvent is an aromatic hydrocarbon petroleum fraction.

9. The process of claim 8, wherein the aromatic hydrocarbon petroleum fraction has a boiling range of 170°–200°C.

10. The process of claim 1, wherein the inert organic solvent is a liquid ether.

11. The process of claim 10, wherein the liquid ether is an aryl-alkyl ether.

12. The process of claim 11, wherein the aryl-alkyl ether is anisole, phenetol, hydroquinone dimethyl ether or resorcinol dimethyl ether.

13. The process of claim 10, wherein the ether is an aliphatic ether.

14. The process of claim 13, wherein the aliphatic ether is a glycol ether.

15. The process of claim 14, wherein the glycol ether is monoethyl diethylene glycol.

16. The process of claim 1, wherein the inert organic solvent is a liquid carboxylic acid ester.

17. The process of claim 16, wherein the liquid carboxylic acid ester is ethyl benzoate.

18. The process of claim 1, wherein the hydrogenation catalyst comprises a noble metal catalyst.

19. The process of claim 18, wherein the noble metal catalyst is platinum or palladium.

20. The process of claim 19, wherein the catalyst is palladium on a carrier of active charcoal.

21. The process of claim 1, wherein the hydrogenation is effected at a temperature of between 80° and 160°C.

22. The process of claim 1, wherein said ratio is between 20:1 to 1:1.

23. The process of claim 1, wherein the amount of catalyst employed is between 0.1 and 5 percent of the weight of the nitroanthraquinone.

* * * * *